(12) United States Patent
Kharait

(10) Patent No.: US 11,285,105 B2
(45) Date of Patent: Mar. 29, 2022

(54) COMPOSITIONS AND METHODS FOR IMPROVING GASTROINTESTINAL ABSORPTION OF ELECTROLYTES

(71) Applicant: IGH NATURALS, INC., Rocklin, CA (US)

(72) Inventor: Sourabh Kharait, Roseville, CA (US)

(73) Assignee: IGH NATURALS, INC., Rocklin, CA (US)

( * ) Notice: Subject to any disclaimer, the term of this patent is extended or adjusted under 35 U.S.C. 154(b) by 0 days.

(21) Appl. No.: 16/941,385

(22) Filed: Jul. 28, 2020

(65) Prior Publication Data

US 2022/0031613 A1 Feb. 3, 2022

(51) Int. Cl.

| | | |
|---|---|---|
| *A61K 9/08* | (2006.01) | |
| *A61K 31/702* | (2006.01) | |
| *A61K 33/06* | (2006.01) | |
| *A61K 47/42* | (2017.01) | |
| *A61K 47/14* | (2017.01) | |
| *A61K 33/42* | (2006.01) | |
| *A61K 9/00* | (2006.01) | |

(52) U.S. Cl.
CPC ............... *A61K 9/08* (2013.01); *A61K 31/702* (2013.01); *A61K 33/06* (2013.01); *A61K 33/42* (2013.01); *A61K 47/14* (2013.01); *A61K 47/42* (2013.01); *A61K 9/0053* (2013.01)

(58) Field of Classification Search
CPC ........ A61K 9/08; A61K 31/702; A61K 33/06; A61K 33/42; A61K 47/14; A61K 47/42; A61K 9/0053
See application file for complete search history.

(56) References Cited

U.S. PATENT DOCUMENTS

| | | | |
|---|---|---|---|
| 4,312,856 A | 1/1982 | Korduner et al. | |
| 10,695,358 B2* | 6/2020 | Chow | ................ A61K 31/7004 |
| 2016/0256479 A1 | 9/2016 | Duska-McEwen et al. | |
| 2016/0339046 A1* | 11/2016 | Chow | ................ A61K 33/30 |
| 2018/0104279 A1* | 4/2018 | Elster | ................ A23L 33/19 |

FOREIGN PATENT DOCUMENTS

| | | |
|---|---|---|
| CN | 100420394 C | 9/2008 |
| CN | 107927788 A | 4/2018 |
| CN | 108308477 A | 7/2018 |
| WO | WO 2020/127161 A1 | 6/2020 |

OTHER PUBLICATIONS

Nakhla et al. Neutral oligosaccharide content of preterm human milk. British Journal of Nutrition (1999), 82, 361-367. (Year: 1999).*
Wang et al. Neutral Human Milk Oligosaccharides Are Associated with Multiple Fixed and Modifiable Maternal and Infant Characteristics. Nutrients 2020, 12(3), 826 (published Mar. 20, 2020). (Year: 2020).*
Nutrition During Lactation. National Academy Press, Washington, D.C. 1991, Committee on Nutritional Status During Pregnancy and Lactation, Institute of Medicine, National Academy of Sciences, ISBN: 0-309-53767-3, 326 pages; Table 6.1. (Year: 1991).*
International Search Report and Written Opinion of the International Searching Authority for International Application No. PCT/US21/70960, International Filing Date Jul. 27, 2021, Date of Mailing of International Search Report Nov. 5, 2021, (9 pages).

* cited by examiner

*Primary Examiner* — Robert A Wax
*Assistant Examiner* — Olga V. Tcherkasskaya
(74) *Attorney, Agent, or Firm* — Sheppard Mullin Richter & Hampton LLP

(57) ABSTRACT

The present disclosure relates generally to compositions and methods for improving gastrointestinal absorption function and correct deficiencies by preserving intestinal epithelial absorptive function. In particular, the compositions and methods for useful for improving gastrointestinal absorption of electrolytes.

10 Claims, No Drawings

COMPOSITIONS AND METHODS FOR IMPROVING GASTROINTESTINAL ABSORPTION OF ELECTROLYTES

BACKGROUND

A strong cellular lining is important for a healthy gastrointestinal (GI) track, as it provides a barrier to the billions of microbes and harmful toxins to which the GI tract is exposed. The intestinal epithelial cells (IECs) form a selective permeability barrier separating luminal content from underlying tissues. The gastrointestinal epithelial lining consists of a monolayer of columnar cells. This monolayer of IECs is constantly moving at a speed of 5-10 µm/h and is renewed every 2-5 days. The maintenance of this barrier is critical for normal growth, development, and disease prevention. Normally, IECs function as a barrier that prevents undesirable solutes, microorganisms, viruses, and luminal antigens from entering the body.

Several elements that participate in the barrier function include the epithelial cells themselves along with tight junctions, adherens junctions, and luminal secretions such as mucus or unstirred layers on the apical aspects of the epithelium. The junctions function as semi-permeable gates that regulate the passive movement of luminal fluid and solutes through the paracellular pathway, and limit passive diffusion of proteins and lipids between the outer leaflet of the apical and basolateral plasma membrane domains. Major transmembrane proteins in the junctions include occludin, claudins, junctional adhesion molecules (JAMs), coxsackie adenovirus receptor (CAR), and E-cadherin.

The epithelium of the GI track, however, is often damaged by infection and inflammation or upon exposure to toxins. This manifests, frequently, with diarrhea and leads to fluid and electrolyte losses through the GI tract. Thus, it is important to maintain the integrity of the gastrointestinal epithelium, and improving its health and absorptive function once the integrity is compromised after injury.

SUMMARY

The present disclosure, in one embodiment, provides compositions and methods for improving gastrointestinal absorption function and correct deficiencies by preserving intestinal epithelial absorptive function. In particular, the compositions and methods for useful for improving gastrointestinal absorption of electrolytes.

One embodiment of the disclosure provides a drinkable aqueous solution, comprising about 0.01% to 12% w/v of one or more oligosaccharides, at least 100 mg/L of one or more electrolytes, and water. Non-limiting examples of the one or more oligosaccharides include 2'-fucosyllactose (2'-FL), 3'-sialyllactose (3'-SL), 6'-sialyllactose (6'-SL), Lacto-N-tetraose, monofucosyllacto-N-hexaose, Lacto-N-fucopentaose (LNFP) and lacto-N-neotetraose (LNnT). LNFP may be selected from the group consisting of LNFP I, LNFP II, LNFP III, LNFP IV and combinations thereof.

In some embodiments, the solution comprises about 0.1% to 5% w/v of the one or more oligosaccharides. In some embodiments, the solution comprises about 0.2% to 2% w/v of the one or more oligosaccharides.

In some embodiments, the one or more oligosaccharides comprise 2'-fucosyllactose (2'-FL), 3'-sialyllactose (3'-SL), or the combination thereof.

In some embodiments, the solution includes less than about 0.5% w/v proteins, or less than about 0.1% w/v proteins. In some embodiments, the solution includes less than about 0.5% w/v lipids, or less than about 0.1% w/v lipids.

Also provided, in some embodiments, is a solid composition obtainable by drying the solution of the present disclosure, or a solid composition suitable for preparing the solution of the present disclosure.

In some embodiments, provided is a method for improving a mammalian subject's absorption of electrolytes, comprising administering to the mammalian subject the solution of the present disclosure. In some embodiments, the subject has gastrointestinal absorption deficiency or suffers from gastrointestinal epithelial injury.

DETAILED DESCRIPTION

The following description sets forth exemplary embodiments of the present technology. It should be recognized, however, that such description is not intended as a limitation on the scope of the present disclosure but is instead provided as a description of exemplary embodiments.

The instant inventor has made the unexpected discovery that complex oligosaccharides derived from mammalian milk (or from plants and fruits) can improve gastrointestinal absorption of electrolytes and correct deficiencies. Such complex oligosaccharides, it is contemplated, can preserve or improve intestinal epithelial absorptive functions.

In accordance with one embodiment of the present disclosure, therefore, provided is a drinkable aqueous solution that includes one or more oligosaccharides, one or more electrolytes, and water. The one or more oligosaccharides are preferably derived from mammalian milk, plant milk, or fruit milk.

Oligosaccharides (OS) are carbohydrates that contain 3 to 10 monosaccharides covalently linked through glycosidic bonds. Human milk contains approximately 7 g of carbohydrates per 100 ml, 90% being lactose, the rest being oligosaccharides. The following principal components (monomers) of oligosaccharides are found in human milk: D-glucose (Glc), D-galactose (Gal), Nacetylglucosamine (GlcNAc), L-fucose (Fuc), N-acetyl neuraminic acid (NeuAc), and N-glycolylneuraminic acid (NeuGc). These components combine in different ways to form 130 different oligosaccharides.

Examples of oligosaccharides found in various types of milk include, without limitation, a-2'-fucosyl-lactose (2'FL), a-3'-galactosyl-lactose (α-3'GL), 3'-galactosyllactose (β-3'GL), 6'-galactosyllactose (β6'GL), Fucosyl-Lactosamine, 3'-N-acetylneuraminyllactose (3'-SL), 6'-N-acetylneuraminyllactose (6'-SL), 6'-N-glycolylneuraminyllactose (6'-SL-NGc/NGL), 6'-Sialyl-lactosamine-glycolyl-Neura (6'-SLN/6'-SLacNAc), Diasylyl-Lactose (DSL), N-acetylglucosaminyl-lactose (NAL), Glycolyl-neuramyl-lactosamine, N-acetyl-glucosaminyl-hexosyl-lactose (NAHL), N-Di-N-acetyl-glucosaminyl-lactose (DNAL), 3'-Sialyl-6'-galactosyl-lactose (3-SHL), 6'-Sialyl-6'-galactosyl-lactose (6-SHL), N-Glycolyl-neuraminyl-hexosyl-lactose (SNGHL), Sialyl-N-acetylglucosaminyl-lactose, Lacto-N-fuco-pentaose III (LNFPIII), Lacto-N-fuco-pentaose V (LNFPIV), N-Acetyl-glucosaminyl-dihexosyl-lactose (NADHL), N-glycolyl-neuraminyl-lactose (DNGL), Sialyl-dihexasyl-lactose (SDHL), and Lacto-N-hexaose (LNH). In some embodiments, any of these is suitable for inclusion in the presently disclosed composition.

In some embodiments, the oligosaccharides include 2'-fucosyllactose (2'-FL), 3'-sialyllactose (3'-SL), 6'-sialyllactose (6'-SL), Lacto-N-tetraose, monofucosyllacto-N-hexaose, lacto-N-neotetraose (LNnT) and various Lacto-N-fucopentaose (LNFP) species, such as LNFP I, LNFP II, LNFP III, and LNFP IV.

In some embodiments, the solution includes about 0.01% to 12% w/v of the oligosaccharides. In some embodiments, the solution includes at least about 0.001%, 0.005%, 0.01%, 0.02%, 0.03%, 0.04%, 0.05%, 0.06%, 0.07%, 0.08%, 0.09%, 0.1%, 0.15%, 0.2%, 0.3%, 0.4%, 0.5%, 0.6%, 0.7%, 0.8%, 0.9%, 1%, 1.1%, 1.2%, 1.3%, 1.4%, 1.5%, 2%, 2.5%, 3%, 3.5%, 4%, 4.5%, 5%, 6%, 7%, 8%, 9% or 10% w/v of the oligosaccharides. In some embodiments, the solution includes no more than about 1%, 1.1%, 1.2%, 1.3%, 1.4%, 1.5%, 2%, 2.5%, 3%, 3.5%, 4%, 4.5%, 5%, 6%, 7%, 8%, 9%, 10%, 11%, 12%, 13%, 14%, 15%, 16%, 17%, 18%, 19%, 20% or 25% w/v of the oligosaccharides.

In some embodiments, the solution includes about 0.01% to 12% w/v of the 2'-FL. In some embodiments, the solution includes at least about 0.001%, 0.005%, 0.01%, 0.02%, 0.03%, 0.04%, 0.05%, 0.06%, 0.07%, 0.08%, 0.09%, 0.1%, 0.15%, 0.2%, 0.3%, 0.4%, 0.5%, 0.6%, 0.7%, 0.8%, 0.9%, 1%, 1.1%, 1.2%, 1.3%, 1.4%, 1.5%, 2%, 2.5%, 3%, 3.5%, 4%, 4.5%, 5%, 6%, 7%, 8%, 9% or 10% w/v of the 2'-FL. In some embodiments, the solution includes no more than about 1%, 1.1%, 1.2%, 1.3%, 1.4%, 1.5%, 2%, 2.5%, 3%, 3.5%, 4%, 4.5%, 5%, 6%, 7%, 8%, 9%, 10%, 11%, 12%, 13%, 14%, 15%, 16%, 17%, 18%, 19%, 20% or 25% w/v of the 2'-FL.

In some embodiments, the solution includes about 0.01% to 12% w/v of the 3'-SL. In some embodiments, the solution includes at least about 0.001%, 0.005%, 0.01%, 0.02%, 0.03%, 0.04%, 0.05%, 0.06%, 0.07%, 0.08%, 0.09%, 0.1%, 0.15%, 0.2%, 0.3%, 0.4%, 0.5%, 0.6%, 0.7%, 0.8%, 0.9%, 1%, 1.1%, 1.2%, 1.3%, 1.4%, 1.5%, 2%, 2.5%, 3%, 3.5%, 4%, 4.5%, 5%, 6%, 7%, 8%, 9% or 10% w/v of the 3'-SL. In some embodiments, the solution includes no more than about 1%, 1.1%, 1.2%, 1.3%, 1.4%, 1.5%, 2%, 2.5%, 3%, 3.5%, 4%, 4.5%, 5%, 6%, 7%, 8%, 9%, 10%, 11%, 12%, 13%, 14%, 15%, 16%, 17%, 18%, 19%, 20% or 25% w/v of the 3'-SL.

In some embodiments, the solution includes about 0.01% to 12% w/v of the 6'-SL. In some embodiments, the solution includes at least about 0.001%, 0.005%, 0.01%, 0.02%, 0.03%, 0.04%, 0.05%, 0.06%, 0.07%, 0.08%, 0.09%, 0.1%, 0.15%, 0.2%, 0.3%, 0.4%, 0.5%, 0.6%, 0.7%, 0.8%, 0.9%, 1%, 1.1%, 1.2%, 1.3%, 1.4%, 1.5%, 2%, 2.5%, 3%, 3.5%, 4%, 4.5%, 5%, 6%, 7%, 8%, 9% or 10% w/v of the 6'-SL. In some embodiments, the solution includes no more than about 1%, 1.1%, 1.2%, 1.3%, 1.4%, 1.5%, 2%, 2.5%, 3%, 3.5%, 4%, 4.5%, 5%, 6%, 7%, 8%, 9%, 10%, 11%, 12%, 13%, 14%, 15%, 16%, 17%, 18%, 19%, 20% or 25% w/v of the 6'-SL.

In some embodiments, the solution includes about 0.01% to 12% w/v of the Lacto-N-neotetraose. In some embodiments, the solution includes at least about 0.001%, 0.005%, 0.01%, 0.02%, 0.03%, 0.04%, 0.05%, 0.06%, 0.07%, 0.08%, 0.09%, 0.1%, 0.15%, 0.2%, 0.3%, 0.4%, 0.5%, 0.6%, 0.7%, 0.8%, 0.9%, 1%, 1.1%, 1.2%, 1.3%, 1.4%, 1.5%, 2%, 2.5%, 3%, 3.5%, 4%, 4.5%, 5%, 6%, 7%, 8%, 9% or 10% w/v of the Lacto-N-neotetraose. In some embodiments, the solution includes no more than about 1%, 1.1%, 1.2%, 1.3%, 1.4%, 1.5%, 2%, 2.5%, 3%, 3.5%, 4%, 4.5%, 5%, 6%, 7%, 8%, 9%, 10%, 11%, 12%, 13%, 14%, 15%, 16%, 17%, 18%, 19%, 20% or 25% w/v of the Lacto-N-neotetraose.

In some embodiments, the solution includes about 0.01% to 12% w/v of the Lacto-N-tetraose. In some embodiments, the solution includes at least about 0.001%, 0.005%, 0.01%, 0.02%, 0.03%, 0.04%, 0.05%, 0.06%, 0.07%, 0.08%, 0.09%, 0.1%, 0.15%, 0.2%, 0.3%, 0.4%, 0.5%, 0.6%, 0.7%, 0.8%, 0.9%, 1%, 1.1%, 1.2%, 1.3%, 1.4%, 1.5%, 2%, 2.5%, 3%, 3.5%, 4%, 4.5%, 5%, 6%, 7%, 8%, 9% or 10% w/v of the Lacto-N-tetraose. In some embodiments, the solution includes no more than about 1%, 1.1%, 1.2%, 1.3%, 1.4%, 1.5%, 2%, 2.5%, 3%, 3.5%, 4%, 4.5%, 5%, 6%, 7%, 8%, 9%, 10%, 11%, 12%, 13%, 14%, 15%, 16%, 17%, 18%, 19%, 20% or 25% w/v of the Lacto-N-tetraose.

In some embodiments, the solution includes about 0.01% to 12% w/v of the monofucosyllacto-N-hexaose. In some embodiments, the solution includes at least about 0.001%, 0.005%, 0.01%, 0.02%, 0.03%, 0.04%, 0.05%, 0.06%, 0.07%, 0.08%, 0.09%, 0.1%, 0.15%, 0.2%, 0.3%, 0.4%, 0.5%, 0.6%, 0.7%, 0.8%, 0.9%, 1%, 1.1%, 1.2%, 1.3%, 1.4%, 1.5%, 2%, 2.5%, 3%, 3.5%, 4%, 4.5%, 5%, 6%, 7%, 8%, 9% or 10% w/v of the monofucosyllacto-N-hexaose. In some embodiments, the solution includes no more than about 1%, 1.1%, 1.2%, 1.3%, 1.4%, 1.5%, 2%, 2.5%, 3%, 3.5%, 4%, 4.5%, 5%, 6%, 7%, 8%, 9%, 10%, 11%, 12%, 13%, 14%, 15%, 16%, 17%, 18%, 19%, 20% or 25% w/v of the monofucosyllacto-N-hexaose.

In some embodiments, the solution includes about 0.01% to 12% w/v of the LNnT. In some embodiments, the solution includes at least about 0.001%, 0.005%, 0.01%, 0.02%, 0.03%, 0.04%, 0.05%, 0.06%, 0.07%, 0.08%, 0.09%, 0.1%, 0.15%, 0.2%, 0.3%, 0.4%, 0.5%, 0.6%, 0.7%, 0.8%, 0.9%, 1%, 1.1%, 1.2%, 1.3%, 1.4%, 1.5%, 2%, 2.5%, 3%, 3.5%, 4%, 4.5%, 5%, 6%, 7%, 8%, 9% or 10% w/v of the LNnT. In some embodiments, the solution includes no more than about 1%, 1.1%, 1.2%, 1.3%, 1.4%, 1.5%, 2%, 2.5%, 3%, 3.5%, 4%, 4.5%, 5%, 6%, 7%, 8%, 9%, 10%, 11%, 12%, 13%, 14%, 15%, 16%, 17%, 18%, 19%, 20% or 25% w/v of the LNnT.

In some embodiments, the solution includes about 0.01% to 12% w/v of the LNFP. In some embodiments, the solution includes at least about 0.001%, 0.005%, 0.01%, 0.02%, 0.03%, 0.04%, 0.05%, 0.06%, 0.07%, 0.08%, 0.09%, 0.1%, 0.15%, 0.2%, 0.3%, 0.4%, 0.5%, 0.6%, 0.7%, 0.8%, 0.9%, 1%, 1.1%, 1.2%, 1.3%, 1.4%, 1.5%, 2%, 2.5%, 3%, 3.5%, 4%, 4.5%, 5%, 6%, 7%, 8%, 9% or 10% w/v of the LNFP. In some embodiments, the solution includes no more than about 1%, 1.1%, 1.2%, 1.3%, 1.4%, 1.5%, 2%, 2.5%, 3%, 3.5%, 4%, 4.5%, 5%, 6%, 7%, 8%, 9%, 10%, 11%, 12%, 13%, 14%, 15%, 16%, 17%, 18%, 19%, 20% or 25% w/v of the LNFP. Examples of LNFP species include LNFP I, LNFP II, LNFP III, and LNFP IV.

The oligosaccharides may be extracted from milk, in some embodiments. One or more of the oligosaccharides, in some embodiments, may be obtained from other sources or synthesized, without limitation.

When the oligosaccharides are obtained from milk, in some embodiments, certain other components in the milks are removed. In some embodiments, therefore, the solution does not include certain amount of protein, fiber, or fat. The following table lists some major components of various types of milk.

TABLE 1

Major components of milk from different sources

| Nutrient (per 100 ml) | Cow milk (whole) | Soy milk (calcium added) | Almond milk | Oat milk | Human milk |
|---|---|---|---|---|---|
| Protein (g) | 3.2 | 2.9 | 0.64 | 1.2 | 1.1 |
| Fat (g) | 3.3 | 1.6 | 1.2 | 2.1 | 4.2 |

TABLE 1-continued

Major components of milk from different sources

| Nutrient (per 100 ml) | Cow milk (whole) | Soy milk (calcium added) | Almond milk | Oat milk | Human milk |
|---|---|---|---|---|---|
| Carbohydrates (g) | 4.8 | 1.7 | 0.63 | 6.6 | 7.5 |
| Calcium (mg) | 114 | 124 | 212 | 144 | 30 |
| Potassium (mg) | 133 | 120 | 72 | 160 | 55 |
| Sodium (mg) | 43 | 37 | 77 | 58 | 15 |
| Cholesterol (mg) | 10 | 0 | 0 | 0 | 14 |

In some embodiments, the solution includes less than about 1% w/v of proteins. In some embodiments, the solution includes less than about 0.9%, 0.8%, 0.7%, 0.6%, 0.5%, 0.4%, 0.3%, 0.2%, 0.15%, 0.1%, 0.05%, 0.02%, 0.01%, 0.005%, or 0.001% w/v of proteins.

In some embodiments, the solution includes less than about 1% w/v of fat (or lipids). In some embodiments, the solution includes less than about 0.9%, 0.8%, 0.7%, 0.6%, 0.5%, 0.4%, 0.3%, 0.2%, 0.15%, 0.1%, 0.05%, 0.02%, 0.01%, 0.005%, or 0.001% w/v of fat (or lipids).

In some embodiments, the solution includes less than about 1% w/v of cholesterol. In some embodiments, the solution includes less than about 0.9%, 0.8%, 0.7%, 0.6%, 0.5%, 0.4%, 0.3%, 0.2%, 0.15%, 0.1%, 0.05%, 0.02%, 0.01%, 0.005%, or 0.001% w/v of cholesterol.

As provided, in conditions where the gastrointestinal epithelium is injured, oral electrolyte solutions may not be effectively absorbed. The presently disclosed solution, however, can help a subject absorb the electrolytes. In some embodiments, the solution contains 20 to 400 mg $Mg^{2+}$, or alternatively 30 to 400 mg $Mg^{2+}$, 40 to 400 mg $Mg^{2+}$, 50 to 400 mg $Mg^{2+}$, 50 to 350 mg $Mg^{2+}$, 50 to 300 mg $Mg^{2+}$, 50 to 250 mg $Mg^{2+}$, 50 to 200 mg $Mg^{2+}$, 50 to 150 mg $Mg^{2+}$, 75 to 400 mg $Mg^{2+}$, 75 to 300 mg $Mg^{2+}$, 75 to 250 mg $Mg^{2+}$, 75 to 200 mg $Mg^{2+}$, 75 to 150 mg $Mg^{2+}$, or 75 to 125 mg $Mg^{2+}$, per 16 fluid ounces (473 mL) of the solution. The magnesium ion can be provided as a salt of magnesium, such as magnesium citrate, magnesium chloride, without limitation.

In some embodiments, the solution contains 40 to 800 mg/L $Mg/L^{2+}$, or alternatively 60 to 800 mg/L $Mg^{2+}$, 80 to 800 mg/L $Mg^{2+}$, 100 to 800 mg/L $Mg^{2+}$, 100 to 700 mg/L $Mg^{2+}$, 100 to 600 mg/L $Mg^{2+}$, 100 to 500 mg/L $Mg^{2+}$, 100 to 400 mg/L $Mg^{2+}$, 100 to 300 mg/L $Mg^{2+}$, 150 to 800 mg/L $Mg^{2+}$, 150 to 600 mg/L $Mg^{2+}$, 150 to 500 mg/L $Mg^{2+}$, 150 to 400 mg/L $Mg^{2+}$, 150 to 300 mg/L $Mg^{2+}$, or 150 to 250 mg/L $Mg^{2+}$.

In some embodiments, the solution contains about 50 to 800 mg $Na^+$, or alternatively 60 to 700 mg $Na^+$, 70 to 600 mg $Na^+$, 80 to 500 mg $Na^+$, 90 to 400 mg $Na^+$, 100 to 300 mg $Na^+$, 100 to 250 mg $Na^+$, 100 to 225 mg $Na^+$, 100 to 200 mg $Na^+$, 125 to 300 mg $Na^+$, 150 to 300 mg $Na^+$, 175 to 300 mg $Na^+$, 125 to 250 mg $Na^+$, 150 to 250 mg $Na^+$, or 175 to 225 mg $Na^+$, per 16 fluid ounces (473 mL) of the solution. The sodium ion can be provided as a salt of sodium, such as sodium citrate, sodium chloride, without limitation.

In some embodiments, the solution contains about 100 to 1600 mg/L $Na^+$, or alternatively 120 to 1400 mg/L $Na^+$, 140 to 1200 mg/L $Na^+$, 160 to 1000 mg/L $Na^+$, 180 to 800 mg/L $Na^+$, 200 to 600 mg/L $Na^+$, 200 to 500 mg/L $Na^+$, 200 to 445 mg/L $Na^+$, 200 to 400 mg/L $Na^+$, 250 to 600 mg/L $Na^+$, 300 to 600 mg/L $Na^+$, 350 to 600 mg/L $Na^+$, 250 to 500 mg/L $Na^+$, 300 to 500 mg/L $Na^+$, or 350 to 445 mg/L $Na^+$.

In some embodiments, the solution contains about 40 to 400 mg $K^+$, or alternatively 50 to 375 mg $K^+$, 60 to 350 mg $K^+$, 70 to 300 mg $K^+$, 80 to 275 mg $K^+$, 90 to 250 mg $K^+$, 100 to 200 mg $K^+$, 110 to 200 mg $K^+$, 120 to 200 mg $K^+$, 130 to 200 mg $K^+$, 140 to 200 mg $K^+$, 150 to 200 mg $K^+$, 100 to 190 mg $K^+$, 100 to 180 mg $K^+$, 100 to 170 mg $K^+$, 100 to 160 mg $K^+$, 110 to 190 mg $K^+$, 120 to 180 mg $K^+$, 130 to 170 mg $K^+$, 140 to 160 mg $K^+$, or 145 to 155 mg $K^+$, per 16 fluid ounces (473 mL) of the solution. The potassium ion can be provided as a salt of potassium, such as potassium citrate, potassium chloride, without limitation.

In some embodiments, the solution contains about 80 to 800 mg/L $K^+$, or alternatively 100 to 750 mg/L $K^+$, 120 to 700 mg/L $K^+$, 140 to 600 mg/L $K^+$, 160 to 550 mg/L $K^+$, 180 to 500 mg/L $K^+$, 200 to 400 mg/L $K^+$, 220 to 400 mg/L $K^+$, 240 to 400 mg/L $K^+$, 260 to 400 mg/L $K^+$, 280 to 400 mg/L $K^+$, 300 to 400 mg/L $K^+$, 200 to 380 mg/L $K^+$, 200 to 360 mg/L $K^+$, 200 to 340 mg/L $K^+$, 200 to 320 mg/L $K^+$, 220 to 380 mg/L $K^+$, 240 to 360 mg/L $K^+$, 260 to 340 mg/L $K^+$, 280 to 320 mg/L $K^+$, or 290 to 310 mg/L $K^+$.

In some embodiments, the solution has an osmolarity below 250 mosmoles per liter (mOsm/L). In some embodiments, the osmolarity is below 240 mOsm/L, 230 mOsm/L, 220 mOsm/L, 210 mOsm/L, 200 mOsm/L, 190 mOsm/L, 180 mOsm/L, 170 mOsm/L, 160 mOsm/L, 150 mOsm/L, 140 mOsm/L, 130 mOsm/L, 120 mOsm/L, 110 mOsm/L, 100 mOsm/L, 90 mOsm/L, 80 mOsm/L, 70 mOsm/L, 60 mOsm/L, 50 mOsm/L, 40 mOsm/L, 30 mOsm/L, 20 mOsm/L, 15 mOsm/L, 10 mOsm/L, 9 mOsm/L, 8 mOsm/L, 7 mOsm/L, 6 mOsm/L, 5 mOsm/L, 4 mOsm/L, 3 mOsm/L, 2 mOsm/L, or 1 mOsm/L.

In some embodiments, the osmolarity is higher than 1 mOsm/L, 2 mOsm/L, 5 mOsm/L, 10 mOsm/L, 15 mOsm/L, 20 mOsm/L, 30 mOsm/L, 40 mOsm/L, 50 mOsm/L, 70 mOsm/L, 80 mOsm/L, 90 mOsm/L, or 100 mOsm/L.

The ratio of $Mg^{2+}$ to $K^+$ is preferably from 1:3 to 2:1, or from 1:2 to 2:1, from 2:3 to 1:1, from 1:3 to 3:2, or from 1:3 to 1:1 (w/w). In some embodiments, the ratio of $Mg^{2+}$ to $K^+$ is about 1:1, 1:2, 2:3 or 3:4 (w/w).

The solution can further include other nutrients, amino acids, or flavoring agents such as vitamin C, citric acid, and/or lime/orange flavoring agent.

Solid compositions are also provided. In some embodiments, the solid composition, once dissolved in water, forms the solution of the present disclosure. In some embodiments, the solid composition can be obtained by drying the solution of the present disclosure.

Specific examples of solutions disclosed here include, without limitation, those provided in Tables 2-4 in the experimental examples.

In various embodiments, the solutions disclosed herein can be used in methods for improve hydration and correct electrolyte deficiencies. Hydration and electrolyte supplement can help reducing muscle soreness, fatigue or cramping in a subject in need thereof. The method, in some embodiments, entails orally administering to the subject an effective amount of the solution of the present disclosure.

In some embodiments, the administration follows an intense physical activity by the subject. In one embodiment, the administration is made before an intense physical activity by the subject. In some embodiments, the subject suffers from gastrointestinal absorption deficiency, and/or from gastrointestinal epithelial injury.

In some embodiments, the effective amount is about 1 fluid ounce, 2 fluid ounces, 5 fluid ounces, 10 fluid ounces, 16 fluid ounces, 18 fluid ounces, or 32 fluid ounces, without limitation.

In some embodiments, the subject experiences muscle soreness, fatigue, or cramping. In some embodiments, the subject, following the administration, experiences reduced muscle soreness, fatigue or cramping. In some embodiment, the subject desires the flavor of the solution.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Example 1

Three test samples of electrolyte drinks were prepared with ingredients shown below.

TABLE 2

| Sample A | |
|---|---|
| Ingredient | Amount |
| 2'-fucosyllactose (2'-FL) | 600 mg |
| Magnesium | 80 mg |
| Potassium | 150 mg |
| Sodium | 200 mg |
| Vitamin C | 100 mg |
| Organic sugar | 2000 mg |
| Other ingredients (Stevia, monk fruit, citric acid, natural colors) | vary |
| Water | 8 fl. oz |

Note: Listed are final elemental concentrations of each electrolyte. For instance, 400 mg of sodium chloride contains approximately 200 mg of elemental sodium.

TABLE 3

| Sample B | |
|---|---|
| Ingredient | Amount |
| 2'-fucosyllactose (2'-FL) | 600 mg |
| 3'-sialyllactose (3'-SL) | 75 mg |
| Magnesium | 80 mg |
| Potassium | 150 mg |
| Sodium | 200 mg |
| Vitamin C | 100 mg |
| Organic sugar | 2000 mg |
| Other ingredients (Stevia, monk fruit, citric acid, natural colors) | vary |
| Water | 8 fl. oz |

TABLE 4

| Sample C | |
|---|---|
| Ingredient | Amount |
| 2'-fucosyllactose (2'-FL) | 600 mg |
| 3'-sialyllactose (3'-SL) | 75 mg |
| Potassium (as chloride and phosphate) | 150 mg |
| Phosphorus (as potassium phosphate) | 250 mg |
| Water | 8 fl. oz |

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A drinkable aqueous solution comprising from about 0.5 g/L to about 20 g/L of one or more synthesized oligosaccharides selected from the group consisting of 2'-fucosyllactose, 3'-sialyllactose, 6'-sialyllactose, lacto-N-tetraose, monofucosyllacto-N-hexaose, lacto-N-fucopentaose and lacto-N-neotetraose, 150-800 mg/L of magnesium, 100-1600 mg/L of sodium, 80-800 mg/L of potassium, and water, wherein the aqueous solution does not include more than about 1 g/L of lipids.

2. The solution of claim 1, wherein the lacto-N-fucopentaose is selected from the group consisting of lacto-N-fucopentaose I, lacto-N-fucopentaose II, lacto-N-fucopentaose III, lacto-N-fucopentaose IV and combinations thereof.

3. The solution of claim 1, wherein the one or more synthesized oligosaccharides comprise oligosaccharides selected from the group consisting of 2'-fucosyllactose, 3'-sialyllactose, and combinations thereof.

4. The solution of claim 1, further comprising 100-1000 mg/L of phosphorus and 20-800 mg/L of calcium.

5. The solution of claim 1, which does not include more than about 5 g/L of proteins.

6. The solution of claim 5, which does not include more than about 0.1 g/L of lipids.

7. A solid composition prepared by drying the solution of claim 1.

8. A method for improving a mammalian subject's absorption of electrolytes, comprising orally administering to the mammalian subject the solution of claim 1.

9. The method of claim 8, wherein the subject has gastrointestinal absorption deficiency.

10. The method of claim 8, wherein the subject suffers from gastrointestinal epithelial injury.

* * * * *